United States Patent [19]

Pellegata et al.

[11] 4,320,143
[45] Mar. 16, 1982

[54] FLUORO-PROSTAGLANDINS AND PROCESS FOR THEIR PREPARATION

[75] Inventors: Renato Pellegata; Carmelo Gandolfi, both of Milan, Italy

[73] Assignee: Farmitalia Carlo Erba S.p.A., Milan, Italy

[21] Appl. No.: 9,098

[22] Filed: Feb. 2, 1979

Related U.S. Application Data

[60] Continuation of Ser. No. 833,999, Sep. 16, 1977, abandoned, which is a division of Ser. No. 779,632, Mar. 21, 1977, abandoned, which is a continuation of Ser. No. 667,261, Mar. 15, 1976, abandoned.

[30] Foreign Application Priority Data

Mar. 21, 1975 [IT] Italy ................................ 21493 A/75

[51] Int. Cl.$^3$ .......................................... C07C 177/00
[52] U.S. Cl. .................................... 424/305; 560/118; 560/121; 560/53; 560/60; 562/463; 562/470; 562/500; 562/503; 424/308; 424/317; 542/429; 260/343.3 P; 260/346.22
[58] Field of Search ....................... 560/118; 562/500; 424/305, 317

[56] References Cited

U.S. PATENT DOCUMENTS

| | | | |
|---|---|---|---|
| 3,914,282 | 10/1975 | Pike ..................................... | 260/468 |
| 3,932,463 | 1/1976 | Schaub ............................. | 260/340.7 |
| 3,933,889 | 1/1976 | Magerlin ............................. | 260/408 |
| 3,933,899 | 1/1976 | Nelson ............................... | 260/473 |
| 3,959,346 | 5/1976 | Schneider .......................... | 260/468 |
| 3,962,293 | 6/1976 | Magerlin ............................. | 260/408 |
| 3,966,792 | 6/1976 | Hayashi .............................. | 560/118 |
| 4,035,415 | 7/1977 | Gandolfi ............................. | 562/500 |
| 4,198,430 | 4/1980 | Gandolfi ............................. | 424/305 |

OTHER PUBLICATIONS

Burger, Medicinal Chemistry, pp. 81, 82 (1960).

*Primary Examiner*—Robert Gerstl
*Attorney, Agent, or Firm*—Cushman, Darby & Cushman

[57] ABSTRACT

Fluoro-prostaglandin compounds are disclosed, such as, for instance, 18,19,20-trinor-17-cyclohexyl-13-14-dehydro-16(S,R)-fluoro-PGF$_{2\alpha}$.

The fluoro-prostaglandins of the present invention have the same therapeutical uses as natural prostaglandins, but have the advantage of being resistant to the enzyme 15-prostaglandin dehydrogenase, and also exhibit a more selective therapeutical action. Certain of the compounds of the present invention exhibit very favorable luteolytic and antiulcer activity.

13 Claims, No Drawings

FLUORO-PROSTAGLANDINS AND PROCESS FOR THEIR PREPARATION

CROSS-REFERENCE TO RELATED APPLICATIONS

This is a continuation of our copending application Ser. No. 833,999, filed Sept. 16, 1977, which in turn is a divisional of application Ser. No. 779,632, filed Mar. 21, 1977, which was a continuation of application Ser. No. 667,261 filed Mar. 15, 1976 all of which are now abandoned.

The present invention relates to fluoro-prostaglandins, a process for their preparation, and pharmaceutical compositions containing them.

The compounds of the invention are optically active or racemic prostaglandins of formula (I)

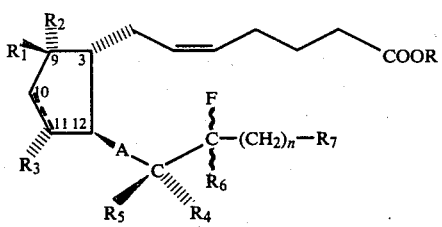

wherein
R is a member selected from the group consisting of hydrogen, a $C_1$-$C_{12}$ alkyl group and a cation of a pharmaceutically acceptable base;
the symbol $\mathrel{\vcenter{\hbox{---}}}$ represents a single or a double bond, wherein, when the symbol $\mathrel{\vcenter{\hbox{---}}}$ is a double bond, $R_3$ is a hydrogen atom and $R_1$ and $R_2$ together form an oxo group, while, when the symbol $\mathrel{\vcenter{\hbox{---}}}$ is a single bond, $R_3$ is hydroxy, and one of $R_1$ and $R_2$ is hydrogen and the other is hydroxy or acyloxy or $R_1$ and $R_2$, taken together, form an oxo group;
A is trans —CH=CH— or —C≡C—; one of $R_4$ and $R_5$ is hydroxy and the other is hydrogen;
$R_6$ is a member selected from the group consisting of hydrogen, methyl and fluorine;
n is zero, or an integer of 1 to 6;
$R_7$, when A is trans —CH=CH—, is a cycloalkyl group containing 3 to 7 ring carbon atoms, while, when A is —C≡C—, $R_7$ is a member selected from the group consisting of methyl, cycloalkyl containing 3 to 7 ring carbon atoms and phenyl unsubstituted or optionally substituted by one or more substituents selected from the group consisting of halogen, $C_1$-$C_6$ alkoxy and trihalomethyl.

The double bond in the 5(6)-position is a cis-double bond.

In the formulae of this specification, the broken lines ( ⫼⫼⫼⫼ ) indicate that the substituents are in the α-configuration, i.e. are below the plane of the ring or of the chain, while the heavy solid lines ( ▬ ) indicate that the substituents are in the β-configuration, i.e. above the plane of the ring or of the chain; the wavy line attachment ( ⸺ ) indicates that the groups may be either in the α-configuration, i.e. below the plane of the ring or of the chain, or in the β-configuration, i.e. above the plane of the ring or of the chain.

As is evident from formula (I), the hydroxy group linked to the carbon atom in the 15 position may be either in the α-configuration

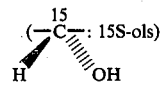

or in the β-configuration

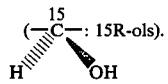

When on the carbon atom in the 16-position there is only one fluorine atom, said substituent may be either a 16S-fluoro (α-configuration) or a 16R-fluoro (β-configuration) or a 16(S,R)-fluoro, i.e. the mixture of the two 16S- and 16R- diastereoisomers. Analogously, when on the carbon atom in 16-position, there is a methyl group, said substituent may be either a 16S-methyl or a 16R-methyl or a 16(S,R)-methyl.

It is also evident that when the symbol $\mathrel{\vcenter{\hbox{---}}}$ represents a double bond and therefore $R_3$ is a hydrogen atom, this hydrogen atom, being linked to a carbon atom which is no more asymmetric, may be obviously in an only one fixed position, i.e. on the plane of the ring, and therefore it may be neither in the α-position (i.e. below the plane of the ring) nor in the β-position (i.e. above the plane of the ring).

The alkyl and alkoxy groups may be branched or straight chain groups.

When R is a $C_1$-$C_{12}$ alkyl group, it is preferably a methyl, ethyl, propyl or heptyl group. Preferably, one of $R_1$ and $R_2$ is hydrogen and the other is hydroxy or $R_1$ and $R_2$, taken together, form an oxo group.

When one of $R_1$ and $R_2$ is acyloxy, it is preferably an alkanoyloxy group containing up to 6 carbon atoms, a benzoyloxy or a p-phenylbenzoyloxy group. When $R_7$ is methyl, n is preferably 3 or 4; when $R_7$ is cycloalkyl or phenyl, n is preferably 1. When $R_7$ is a cycloalkyl group, it is preferably cyclopentyl, cyclohexyl or cycloheptyl.

When $R_7$ is a trihalomethyl-substituted phenyl, the trihalomethyl group is preferably trifluoromethyl or trichloromethyl. Examples of cations of pharmaceutically acceptable bases are either metallic cations, such as sodium, potassium, calcium and aluminium or organic amine cations, such as trialkylamines.

Specific examples of compounds of the invention are the following:
18,19,20-trinor-17-cyclohexyl-16(S,R)-fluoro-PGF$_{2\alpha}$,
18,19,20-trinor-17-cyclohexyl-16(S,R)-fluoro-PGE$_2$,
18,19,20-trinor-17-cyclohexyl-16S-fluoro-PGF$_{2\alpha}$,
18,19,20-trinor-17-cyclohexyl-16R-fluoro-PGF$_{2\alpha}$,
a 16-fluoro-18,19,20-trinor-17-cyclopentyl-PGF$_{2\alpha}$,
a 16-fluoro-18,19,20-trinor-17-cyclopentyl-PGE$_2$,
18,19,20-trinor-17-cyclohexyl-16,16-difluoro-PGF$_{2\alpha}$,
18,19,20-trinor-17-cyclopentyl-16,16-difluoro-PGF$_{2\alpha}$,
a 16-fluoro-13,14-dehydro-PGF$_{2\alpha}$,
a 16-fluoro-13,14-dehydro-PGE$_2$,
a 16-fluoro-13,14-dehydro-PGA$_2$,
a 16-fluoro-13,14-dehydro-PGF$_{2\beta}$,
16S-methyl-16R-fluoro-13,14-dehydro-PGE$_2$,
16R-methyl-16S-fluoro-13,14-dehydro-PGE$_2$,
16S,20-dimethyl-16R-fluoro-13,14-dehydro-PGE$_2$,
16R,20-dimethyl-16S-fluoro-13,14-dehydro-PGE$_2$,
a 16-methyl,16-fluoro-13,14-dehydro-PGF$_{2\alpha}$,
a 16-methyl,16-fluoro-13,14-dehydro-PGF$_{2\beta}$,
a 16-methyl,16-fluoro-13,14-dehydro-PGA$_2$, 16,16-difluoro-13,14-dehydro-PGE$_2$,
16,16-difluoro-13,14-dehydro-PGF$_{2\alpha}$,
16,16-difluoro-13,14-dehydro-PGA$_2$,
18,19,20-trinor-17-cyclohexyl-16(R,S)-fluoro-13,14-dehydro-PGF$_{2\alpha}$,
18,19,20-trinor-17-cyclohexyl-16R-fluoro-13,14-dehydro-PGF$_{2\alpha}$,
18,19,20-trinor-17-cyclohexyl-16S-fluoro-13,14-dehydro-PGF$_{2\alpha}$,
18,19,20-trinor-17-cyclohexyl-16,16-difluoro-13,14-dehydro-PGF$_{2\alpha}$,
a 16-fluoro-18,19,20-trinor-17-cyclopentyl-13,14-dehydro-PGF$_{2\alpha}$,
a 16-fluoro-18,19,20-trinor-17-phenyl-13,14-dehydro-PGF$_{2\alpha}$,
a 16-fluoro-18,19,20-trinor-17-cyclopentyl-13,14-dehydro-PGE$_2$,
a 16-fluoro-18,19,20-trinor-17-cyclohexyl-13,14-dehydro-PGE$_2$,
a 16-fluoro-18,19,20-trinor-17-phenyl-13,14-dehydro-PGE$_2$,
18,19,20-trinor-17-phenyl-16,16-difluoro-13,14-dehydro-PGF$_{2\alpha}$,
18,19,20-trinor-17-cyclopentyl-16,16-difluoro-13,14-dehydro-PGF$_{2\alpha}$,
18,19,20-trinor-17-phenyl-16,16-difluoro-13,14-dehydro-PGE$_2$,
18,19,20-trinor-17-cyclopentyl-16,16-difluoro-13,14-dehydro-PGE$_2$,
18,19,20-trinor-17-cyclohexyl-16,16-difluoro-13,14-dehydro-PGE$_2$, The compounds of formula (I) are prepared by a process comprising reacting an optically active compound, or a racemic mixture of compounds of formula (II)

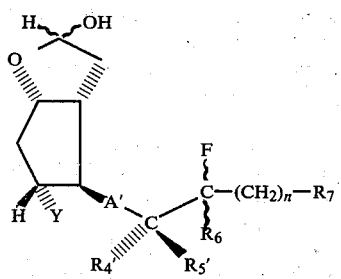

wherein
n, $R_6$ and $R_7$ are as defined above, A' is —C≡C— or —CH=CX—, wherein X is hydrogen or halogen, Y is hydroxy or a known protecting group bound to the ring by an ethereal oxygen atom, and one of $R'_4$ and $R'_5$ is hydroxy or a known protecting group bound to the chain by an ethereal oxygen atom, and the other is a hydrogen atom, with a Wittig reagent comprising the group of formula —(CH$_2$)$_4$—COOR, wherein R is a hydrogen atom or a C$_1$–C$_{12}$ alkyl group, to give a compound of formula (III)

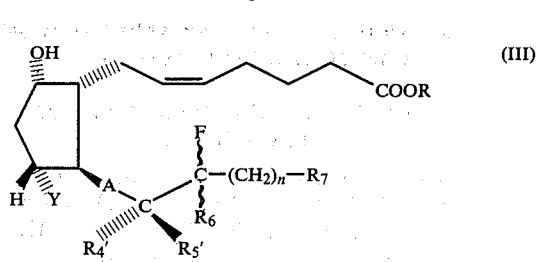

wherein
R, Y, A, R'$_4$, R'$_5$, R$_6$, R$_7$ and n are as defined above, which when Y is a known protecting group as above defined, and one of R'$_4$ and R'$_5$ is a known protecting group as above defined and the other is hydrogen, may be optionally esterified to give the 9α- or 9β-acyloxy derivative, and then, deetherifying the compound of formula (III) wherein Y is a known protecting group as defined above and/or one of R'$_4$ and R'$_5$ is a known protecting group as defined above and the other is hydrogen, or deetherifying the 9α- or 9β-acyloxy derivative of the compound of formula (III), so obtaining a compound of formula (I), wherein R$_3$ is a hydroxy group, the symbol ---- is a single bond, one of R$_1$ and R$_2$ is hydrogen, and the other is hydroxy or acyloxy, and one of R$_4$ and R$_5$ is a hydroxy group and the other is hydrogen, or, if desired, oxidizing the 9α- or 9β-hydroxy group in a compound of formula (IIIa)

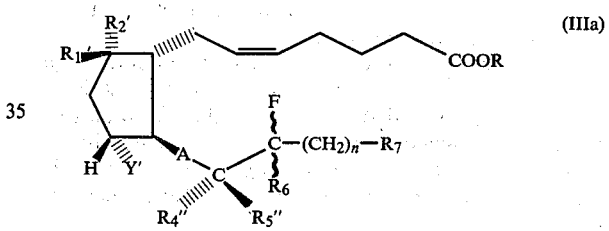

wherein
R, A, R$_6$, R$_7$ and n are as defined above, one of R'$_1$ and R'$_2$ is hydrogen and the other is hydroxy, Y' is a known protecting group as defined above and one of R''$_4$ and R''$_5$ is a known protecting group as defined above and the other is hydrogen, to give a compound of formula (IV)

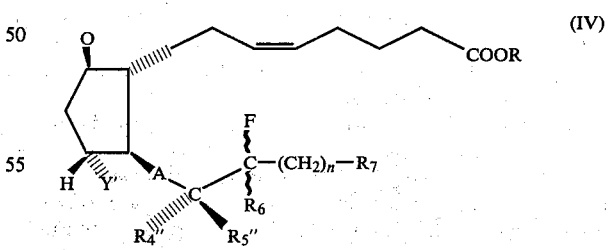

wherein
R, Y', A, R''$_4$, R''$_5$, R$_6$, R$_7$ and n are as defined above, which in turn is deetherified in the 11- and 15- positions to give, according to the reaction conditions used, either a compound of formula (I) wherein the symbol ---- is a single bond, R$_3$ is hydroxy, and R$_1$ and R$_2$, taken together, form an oxo group, or a compound of formula (I) wherein the symbol ---- is a double bond, R$_3$ is hydrogen, and R$_1$ and R$_2$ together form an oxo group, and/or, if desired, reacting a compound of formula (I) wherein R is a hydrogen atom and the hydroxy group in the 11- and/or 15- position is optionally protected as described above, with a base, followed, if required, by deetherification, to give a compound of formula (I) wherein R is a cation, or esterifying a compound of formula (I) wherein R is a hydrogen atom and the hydroxy group in the 11- and/or 15- position is optionally protected as described above, followed, if required, by deetherification, to give a compound of formula (I) wherein R is $C_1$–$C_{12}$ alkyl, or hydrolyzing a compound of formula (I) wherein R is $C_1$–$C_{12}$ alkyl and the hydroxy group in the 11- and/or 15- position is optionally protected as described above, followed, if required, by deetherification to give a compound of formula (I) wherein R is a hydrogen atom. The hydrolysis of a compound of formula (I) wherein $R_1$ and $R_2$ together form an oxo group and R is $C_1$–$C_{12}$ alkyl group, to give a compound of formula (I) wherein $R_1$ and $R_2$ together form an oxo group and R is hydrogen may be also carried out by enzymatic way, e.g. by using a yeast esterase.

The known protecting groups (i.e. ether groups) should be convertible to hydroxy groups under mild reaction conditions, e.g. acid hydrolysis. Examples are acetalic ethers, enolethers and sylylethers. The preferred groups are:

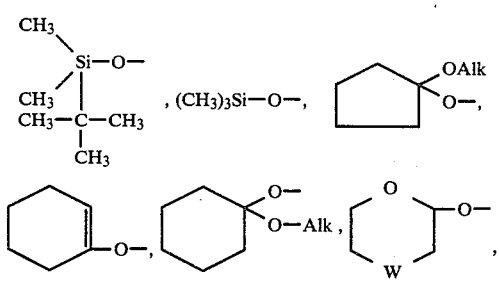

wherein W is —O— or —$CH_2$—, and Alk is a lower alkyl group.

When in the lactol of formula (II) A' is —CH=CH—, it is a trans —CH=CH—. When in the lactol of formula (II) A' is —CH=CX—, wherein X is halogen, preferably chlorine, bromine or iodine, the hydrogen atom linked to the carbon atom in the 13- position and the hydrogen atom linked to the carbon atom in the 14- position, may be either in the trans-position (geometric trans-isomers) or in the cis-position (geometric cis-isomers). Preferably, they are in the trans-position. When in the lactol of formula (II) A' is trans —CH=CH—, compounds of formula (III) wherein A is trans —CH=CH— are obtained; in this case, the Wittig reaction may be performed by using about 2–3 moles of Wittig reagent per mole of lactol and the reaction lasts about one hour.

When in the lactol of formula (II) A' is —C≡C— or —CH=CX— wherein X is halogen, compounds of formula (III) wherein A is —C≡C— are obtained.

When A' is —C≡C— or —CH=CX— wherein X is bromine or iodine, the Wittig reaction may be performed by using about two moles of Wittig reagent per mole of lactol and it is sufficient that the reaction lasts 10–20 minutes. When A' is —CH=CX— wherein X is chlorine, it is necessary, by using for example 1.5 to 2.5 moles of Wittig reagent per mole of lactol, to prolong the reaction time up to 10 hours or, if it is desired to use shorter reaction times, it is necessary to employ a great excess of Wittig reagent (at least 5 moles of Wittig reagent per mole of lactol for reaction time of about 30 minutes).

The Wittig reaction is performed by using the conditions generally followed for this kind of reaction, i.e. in an organic solvent, for example diethylether, hexane, dimethyl sulphoxide, tetrahydrofuran, dimethylformamide or hexamethylphosphoramide, in the presence of a base, preferably sodium hydride and potassium tert. butoxide, at 0° C. to the reflux temperature of the reaction mixture, preferably at room temperature or below.

The term "Wittig reagent" includes compounds of formula

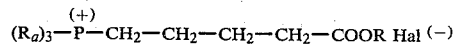

wherein $R_a$ is aryl or alkyl, Hal is bromine or chlorine and R is hydrogen or alkyl. When $R_a$ is alkyl, it is preferably ethyl. The preparation of the Wittig reagent is discussed in detail by Tripett, Quart. Rev., 1963, XVII, No. 4, 406.

When in the lactol of formula (II) A' is —CH=CX—, wherein X is bromine, chlorine or iodine, during the reaction with the Wittig reagent, the dehydrohalogenation takes place as easily when the hydrogen atom linked to the carbon atom in the 13- position and the halogen atom linked to the carbon atom in the 14- position are in the trans-position as when they are in the cis-position. The optional acylation of the 9α- hydroxy group in the compound of formula (III) may be performed in a conventional manner, for example by treatment with an anhydride or a chloride of a carboxylic acid in presence of a base. In this case a 9α- acyloxy derivative is obtained.

On the contrary, when the acylation of the 9α- hydroxy group in the compound of formula (III) is carried out with a carboxylic acid in presence of a compound of formula $M^vY_3$, wherein $M^v$ is a metalloid of the V group and Y is an alkyl, a dialkylamino or an aryl group, and of a hydrogen-acceptor agent, a 9β- acyloxy derivative is obtained, that is, in the latter case, the esterification involves the complete inversion of configuration of the hydroxy group in the 9- position. This reaction is preferably carried out at room temperature in an inert anhydrous solvent, preferably selected from the group consisting of aromatic hydrocarbons, such as benzene and toluene, linear or cyclic ethers, for example diethyl ether, dimethoxyethane, tetrahydrofuran and dioxan. All the used reagents, that are the compounds of formula $W^v Y_3$, the esterifying carboxylic acid and the hydrogen-acceptor agent, are employed in the proportion of at least 1.5 mole per each mole of alcohol; 2 to 4 moles of the reagents per each mole of alcohol are preferably used.

In the compound of formula $M^v Y_3$, $M^v$ is preferably P, As, Sb, especially P. Again in the same compound, when Y is alkyl, it is preferably methyl, while when Y is aryl, it is preferably phenyl; when Y is dialkylamino, it is preferably dimethylamino. The compound of formula $M^v Y_3$ is preferably selected from the group consisting of triphenylphosphine, triphenylarsine, triphenylstibine and hexamethyltriaminophosphine of formula $[(CH_3)_2N]_3P$. The hydrogen-acceptor used is preferably an ester or an amide of the azodicarboxylic acid, preferably ethyl azodicarboxylate, but also other hydrogen-acceptors may be used, for instance 2,3,5,6-tetrachloro-benzoquinone, 2,3-dicyano-5,6-dichlorobenzoquinone or azobisformamide.

The deetherification reaction of the compound of formula (III)—or of the 9α- or 9β-acyloxy derivative of this compound—wherein Y and/or one of R'$_4$ and R'$_5$ are a known protecting group as above defined, is performed under conditions of mild acid hydrolysis, for example with mono- or poly-carboxylic acids, e.g. formic, acetic, oxalic, citric and tartaric acid, and in a solvent, for example water, acetone, tetrahydrofuran, dimethoxyethane and lower aliphatic alcohols. Preferably, 0.1 to 0.25 N poly-carboxylic acid (e.g. oxalic or citric acid) is used in presence of a convenient low boiling co-solvent which is miscible with water and which can be easily removed in vacuo at the end of the reaction.

The oxidation of the 9α- or 9β-hydroxy group to yield an oxo group may be carried out with, for example, Jones reagent or Moffatt reagent.

As stated above, the deetherification of the compound of formula (IV) may give, according to the reaction conditions used, either a compound of formula (I) wherein the symbol ≈≈≈ is a single bond, R$_3$ is hydroxy and R$_1$ and R$_2$, taken together, form an oxo group, or a compound of formula (I) wherein the symbol ≈≈≈ is a double bond, R$_3$ is hydrogen and R$_2$ and R$_3$, taken together, form an oxo group.

The former compound may be obtained as the only product by operating at temperatures ranging between about 25° C. and about 35°–38° C., while by operating at higher temperatures, for example, at the reflux temperature for about three hours, the latter compound is obtained as the only product.

The lactol of formula (II) may be prepared, in turn, by means of a multi-stop process using as starting material an optically active or racemic lactone of formula (V)

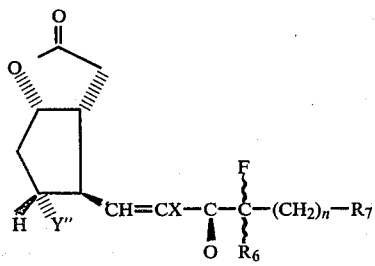

(V)

wherein

Y" is hydroxy, acyloxy or a known protecting group bound to the ring through an ethereal oxygen atom, X, R$_6$, R$_7$, and n are as defined above; and wherein the hydrogen atom linked to the carbon atom in the 13-position and the halogen atom linked to the carbon atom in the 14- position (prostaglandin numbering) may be either in the trans-position or in the cis-position. The multi-step process to prepare the compound of general formula (II) starting from the lactone of formula (V) involves the following steps:

(a) reduction of the 15-oxo group (prostaglandin numbering) of the lactone of formula (V) to yield a mixture of 15S- and 15R-ols having the formulae (VIa) and (VIb)

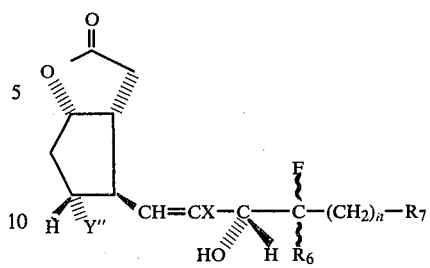

(VIa) (15S-ol)

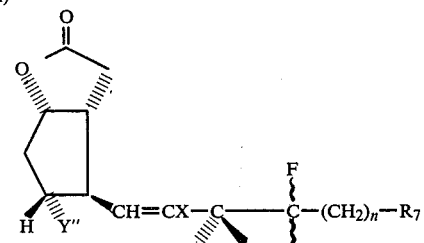

(VIb) (15R-ol)

wherein Y", X, R$_6$, R$_7$, and n are as above defined, followed by the separation of the 15S-ol from the 15R-ol and, if desired, by the dehydrohalogenation of the separated alcohols wherein X is halogen to give a compound of formula (VIIa)

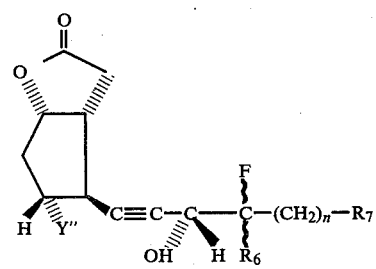

(VIIa)

or a compound of formula (VIIb)

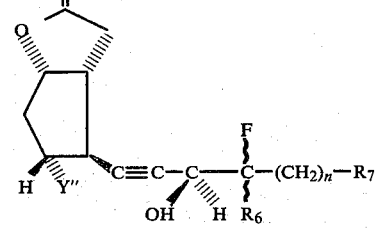

(VIIb)

wherein Y", R$_6$, R$_7$, and n are as above defined. If desired, the reduction may follow the dehydrohalogenation. The reduction of the 15-oxo group may be suitably performed in an organic solvent, such as acetone, diethylether, dimethoxyethane, dioxan, or benzene or their mixtures, by using e.g. metal borohydrides, in particular sodium borohydride, lithium borohydride, zinc borohydride, sodium trimethoxyborohydride.

The separation of the 15S-ol from the 15R-ol may be performed by chromatography, e.g. silica gel chromatography or by fractionated crystallization. The dehydrohalogenation may be performed in a solvent, preferably selected from the group consisting of dimethylsulphoxide, dimethylformamide, hexamethylphosphoramide in presence of a base which may be for example an alkaline metal amide, potassium tert. butylate or the anion

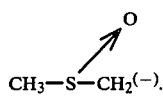

(b) Conversion of a compound of formula (VIII)

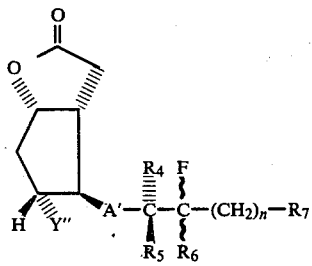

wherein
Y", R$_6$, R$_7$, A', and n are as defined above and one of R$_4$ and R$_5$ is a hydrogen atom and the other is a hydroxy group into a compound of formula (IX)

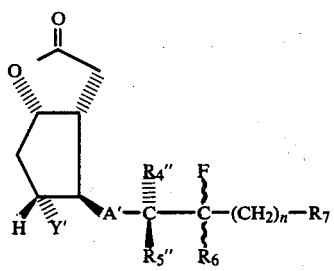

wherein
A', R$_6$, R$_7$, and n are as defined above, Y' is a known protecting group bound to the ring through an ethereal oxygen atom, and one of R"$_4$ and R"$_5$ is a known protecting group bound to the chain by an ethereal oxygen atom and the other is a hydrogen atom. The etherification of the compound of formula (VIII) to give a compound of formula (IX) is preceded when, in the compound of formula (VIII), Y" is an acyloxy group, by saponification for example by mild treatment with an alkali, to give a compound of formula (VIII) wherein Y" is a hydroxy group.

The etherification is preferably carried out with a vinylic ether of formula

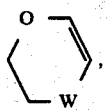

wherein W is —O— or —CH$_2$—, in presence of catalytic amounts of, for example, phosphorus oxychloride, p-toluenesulphonic acid or benzene sulphonic acid, or with a silyl ether, for instance by reacting a trisubstituted chlorosilane in presence of an acceptor base (for example a trialkylamine) of the hydrogen halide formed, or with an enol ether, for instance by reaction, in presence of an acid catalyst with a 1,1-dialkoxy-cyclopentane or cyclohexane, at the reflux temperature in an inert solvent and distilling the alcohol formed to obtain mixed dialkoxy ethers or enol ethers, according to the quantity of catalyst used or the heating time.

(c) Reduction of the compound of formula (IX) to yield a lactol derivative of formula (X)

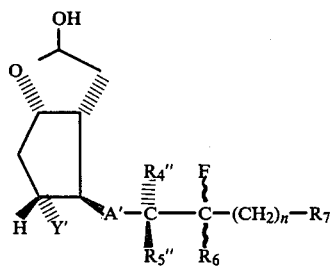

wherein
Y', A', R"$_4$, R"$_5$, R$_6$, R$_7$, and n are as above defined. The reduction may be performed by treatment with diisobutylaluminium hydride or sodium bis-(2-methoxyethoxy)-aluminium hydride in an inert solvent, for example, toluene, n-heptane, n-hexane or benzene or their mixtures, at below 30° C.

(d) Optional deetherification of the compound of formula (X) to give a comound having the free 11- and 15-hydroxy groups. The deetherification may be carried out by mild acid hydrolysis, in a solvent miscible with water, with a solution of a mono- or poly-carboxylic acid.

All the compounds mentioned under items (a) to (d) may be either optically active compounds or racemic mixtures thereof.

The lactone of formula (V) may be in turn prepared in an only one step by reaction of an optically active or racemic aldehyde of formula (XI)

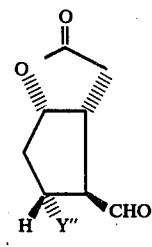

wherein
Y" is as defined above, with an optically active or racemic phosphonate carbanion of formula (XII)

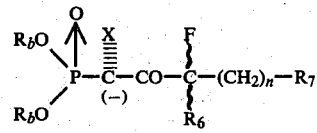

wherein R$_b$ is lower alkyl,
X, R$_6$, R$_7$, and n are as defined above. The reaction is suitably performed in a solvent which is preferably dry benzene, dimethoxyethane, tetrahydrofuran, dimethylformamide or their mixtures, and using a suspension of 1.1–1.2 molar equivalent of the halo-phosphonate carbanion.

When in the aldehyde of formula (XI) Y" is an acyloxy group, it may be for example, acetoxy, propionyloxy, benzoyloxy and p-phenyl-benzoyloxy. When Y'' is a known protecting group bound to the ring through an ethereal oxygen atom, it may be for example one of the ethereal protecting groups reported hereabove.

The aldehyde of formula (XI) may be prepared substantially as described by E. J. Corey et al., Ann. of New York Acad. of Sciences, 180, 24 (1971).

The phosphonate carbanion of formula (XII) may be in turn prepared by reacting a phosphonate of formula (XIII)

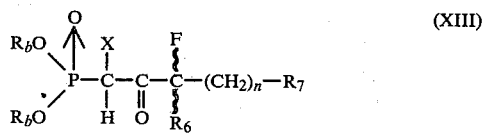

wherein
$R_b$, X, $R_6$, $R_7$, and n are as defined above, with an equivalent of a base preferably selected from the group consisting of sodium hydride, lithium hydride, calcium hydride, an alkyl lithium derivative and the anion $CH_3$—$SO_2$—$CH_2^{(-)}$.

The phosphonate of formula (XIII), wherein X is halogen, may be obtained by halogenation of a phosphonate of formula (XIV)

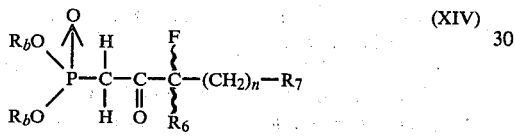

wherein $R_b$, $R_6$, $R_7$, and n are as defined above. The halogenation may be carried out in a conventional manner, operating substantially as in the halogenation of β-ketoesters. The phosphonate of formula (XIV) may be prepared by known methods, e.g. according to E. J. Corey et al., J. Am. Chem. Soc. 90, 3247 (1968) and E. J. Corey and G. K. Kwiatkowsky, J. Am. Chem. Soc., 88, 5654 (1966). Preferably, the phosphonate of formula (XIV) is prepared by reaction of lithium methylphosphonate with a lower alkylester of the optionally substituted aliphatic acid. When the aliphatic acid contains asymmetric carbon atoms, it is possible to use either the racemic acid or one of its optical antipodes. The lower alkyl ester of the optionally substituted aliphatic acid may be prepared by conventional methods.

Alternatively, the phosphonate carbanion of formula (XII) wherein X is halogen may be prepared in situ by reacting a phosphonate carbanion of formula (XII), wherein X is hydrogen, and $R_b$, $R_6$, $R_7$, and n are as defined above, with an equivalent of a halogenating agent selected from the group consisting of N-chloroacetamide, N-chlorosuccinimide, N-bromosuccinimide, N-bromoacetamide, N-bromocaprolactame, N-iodosuccinimide.

In the preparation of the halo-lactone of formula (V), wherein A' is —CH=CX—, according to the hereabove described methods, both compounds wherein the hydrogen atom linked to the carbon atom in the 13-position and the halogen atom linked to the carbon atom in the 14-position (prostaglandin numbering) are in the trans-position (geometric trans-isomers) and compounds wherein said atoms are in the cis-position (geometric cis-isomers) are obtained. The geometric trans-isomers are obtained in a far higher percentage (92–95%), while the geometric cis-isomers are obtained in a far lower percentage (5–8%).

The geometric trans-isomers of formula

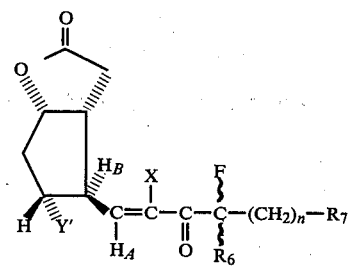

can be easily distinguished from the geometric cis-isomers of formula

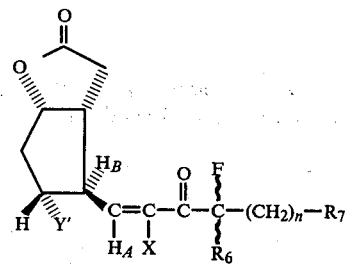

in that the $H_A$ vinylic protons of the two isomers resonate at different positions and the coupling constants of the $H_A$ vinylic proton with the $H_B$ proton are well different (respectively 9 Hz for the trans-isomer and 10.2 Hz for the cis-isomer).

Anyway, both the trans-isomers and the cis-isomers are intermediates for the synthesis of the 13,14-dehydroprostaglandins of the invention.

The lactol of formula (II) wherein A' is —C≡C— may be also prepared by dehydrohalogenation of the lactol of formula (II) wherein A' is

wherein X is bromine, chlorine or iodine. The dehydrohalogenation may be carried out in an aprotic solvent preferably selected from the group consisting of dimethylsulphoxide, dimethylformamide and hexamethylphosphoramide by treatment with a base preferably selected from the group consisting of potassium tert.butylate, an alkali metal amide and the anion $CH_3$—$SO$—$CH_2^{(-)}$.

Among the intermediates described in this specification, the following are compounds of the invention:

(1) a compound of formula (XV)

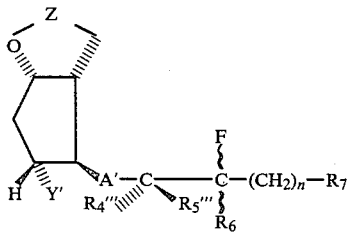

(XV)

wherein Z is

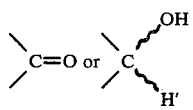

one of $R_4'''$ and $R_5'''$ is hydrogen and the other is hydroxy or a known protecting group bound to the chain by an ethereal oxygen atom or, when Z is $>C=O$, $R_4'''$ and $R_5'''$, taken together, may also be an oxo group, and wherein Y, A', $R_6$ $R_7$ and n are as defined above.

(2) A compound of formula (XVI)

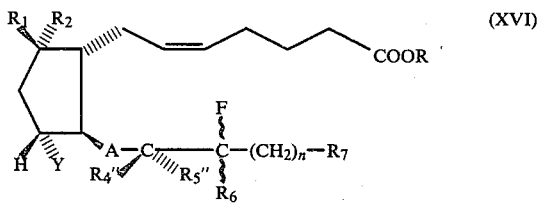

(XVI)

wherein

Y is hydroxy or a known protecting group bound to the ring by an ethereal oxygen atom, one of $R_4''$ and $R_5''$ is a known protecting group bound to the chain by an ethereal oxygen atom and the other is hydrogen, one of $R_1$ and $R_2$ is hydrogen and the other is hydroxy or acyloxy or $R_1$ and $R_2$, taken together, form an oxo group, and R, $R_6$, $R_7$, A, n are as defined above.

The compounds of formula (I) may be used for the same therapeutical indications as natural prostaglandins, with respect to which, however, they offer the advantage of being no substrates for the enzyme 15-prostaglandin dehydrogenase, which, as is known, quickly inactivates natural prostaglandins, and, furthermore, are characterized by a more selective therapeutical action.

The compounds of formula (I), furthermore, competitively inhibit the use of natural prostaglandins as substrate by the same enzyme.

In particular, the compounds of formula (I), wherein $R_2$ and $R_3$ are hydroxy, are provided with an outstanding luteolytic activity, i.e. they are useful as abortive agents, as shown by Table I, from which it results that the presence in $C_{16}$ of a fluorine atom maintains the luteolytic activity unchanged, and, at the same time, reduces the contracturing activity in the uterine muscles, so allowing a dissociation between the two activities, while the compounds of formula (I), wherein $R_1$ and $R_2$, together, form an oxo group, and $R_3$ is hydroxy, are in particular endowed with remarkable luteolytic and anti-ulcer activities, as shown by Table II, from which it results that the presence in $C_{16}$ of a fluorine atom improves the anti-ulcer activity and causes a good luteolytic activity, while it reduces the capacity to stimulate smooth muscles, such as the ileum of guinea-pigs and the uterus of rats.

TABLE I

| Compounds | Potency Ratio Rat Uterus | Abortion in Rats* (number of abortions/ number of rats) |
|---|---|---|
| $PGF_{2\alpha}$ | 1 | 0/10 |
| 18,19,20-trinor-17-cyclohexyl-$PGF_{2\alpha}$ | 3.22 | 7/10 |
| 18,19,20-trinor-17-cyclohexyl-16(S,R)-fluoro-$PGF_{2\alpha}$ | 0.33 | 6/12 |
| 18,19,20-trinor-17-cyclohexyl-13,14-dehydro-$PGF_{2\alpha}$ | 10.59 | 10/10 |
| 18,19,20-trinor-17-cyclohexyl-13,14-dehydro-16(S,R)-fluoro-$PGF_{2\alpha}$ | 3.29 | 10/10 |

*In this and the subsequent antifertility experiments, all the compounds are administered subcutaneously at a dose of 2 mg/kg b.w. (0.2 ml/100 g b.w.) to female rats on the 10th day of pregnancy after inspection of the uterus, and implanted fetuses are counted on the same day. Animals are killed on the 21st day of pregnancy and the presence of any fetal debris is counted as no abortion.

TABLE II

| Compounds | Potency Ratio of Rats | | Anti-ulcer activity | Number of Abortions/ Number of Rats |
|---|---|---|---|---|
| | Ileus | Uterus | | |
| $PGE_2$ | 1 | 1 | 1 | 0/10 |
| 18,19,20-trinor-17-cyclohexyl-$PGE_2$ | 0.27 | 0.75 | 0.40 | 0/10 |
| 18,19,20-trinor-17-cyclohexyl-16(S,R)-fluoro-$PGE_2$ | 0.11 | 0.55 | 1.20 | 10/12 |

The compounds of formula (I) can be administered orally, parenterally, or by intravenous or intrauterine (extra-amniotic or intra-amniotic) way, by rectal suppositories or by inhalation. For example, they can be administered by intravenous infusion of a sterile isotonic saline solution at the rate of 0.01 to 10, preferably 0.05 to 1, μg/kg of mammal body weight per minute.

The invention therefore also provides a pharmaceutical composition comprising a compound of formula (I) and a pharmaceutically acceptable carrier or diluent.

The compositions may be prepared by conventional methods and can be, for example, in the form of tablets, capsules, pills, suppositories or bougies, or in liquid form e.g. solutions, suspensions or emulsions.

Examples of substances which can serve as carriers or diluents are water, gelatin, lactose, starches, magnesium stearate, talc, vegetable oil, benzyl alcohol and cholesterol.

The invention is illustrated by the following examples, where the abbreviations THP, DIOX, DMSO, THF, DMF, DIBA, HMPA, $Et_2O$, DME, respectively, refer to tetrahydropyranyl, dioxanyl, dimethylsulphoxide, tetrahydrofuran, dimethylformamide, diisobutylalluminium hydride, hexamethylenephosphoramide, ethyl ether and dimethoxyethane.

EXAMPLE 1

A suspension of 1.220 g of NaH (80% dispersion in mineral oil) in 30 ml of dry DMSO, under nitrogen and with humidity excluded is heated at 58°–65° C., until no more hydrogen evolves. After cooling to 4°–8° C., 8.92 g of triphenyl-(4-carboxybutyl)-phosphonium bromide is added and the mixture is stirred until it is all dissolved, with formation of a dark red solution of the ylide, maintaining the temperature at about 10°–12° C. by means of outside cooling. To this is added a solution in 5 ml of anhydrous DMSO of 1.2 g of 2-[3α,5α-dihydroxy-(3α-THP-ether)-2β-[(3S)-3-hydroxy-(3-THP-ether)-4(R,S)-fluoro-5-cyclohexyl-trans-1-pentenyl]-1α-cyclopentyl)-ethanal-γ-lactol. The mixture is stirred for 4 hours, then diluted with 30 ml of water and extracted repeatedly (16 times with 5 ml each) with ethyl ether, to remove the triphenylphosphoxide formed. The combined ether extracts are re-extracted with 0.5 N NaOH (5 times with 5 ml) and then discarded. The combined aqueous alkaline extracts are acidified to pH 4.5 with 2 N sulfuric acid and extracted with ethyl ether-pentane 1:1. These organic extracts are combined, washed to neutral and evaporated to dryness, after drying over $Na_2SO_4$, yielding 1.3 g of 7-{3α,5α-dihydroxy-(3-THP-ether)-2β-[(3S)-3-hydroxy-(3-THP-ether)-4(R,S)-fluoro-5-cyclohexyl-trans-1-pentenyl]-1β-cyclopentyl}-5-cis-heptenoic acid [18,19,20-trinor-17-cyclohexyl,16(R,S)-fluoro-$PGF_{2\alpha}$-11,15-bis-THP-ether].

By the same procedure, if one starts with the individual 16S-fluoro and 16R-fluoro isomers as well as with one of the following aldehydes:
2-{3α,5α-dihydroxy-(3α-THP-ether)-2β-[(3S)-3-hydroxy-(3-THP-ether-4(R,S)-fluoro-5-cyclopentyl-trans-1-pentenyl]-1α-cyclopentyl})-ethanal-γ-lactol;
2-{3α,5α-dihydroxy-(3α-THP-ether)-2β-[(3S)-3-hydroxy-(3-THP-ether)-4,4'-difluoro-5-cyclopentyl-trans-1-pentenyl]-1α-cyclopentyl}-ethanal-γ-lactol;
2-{3α,5α-dihydroxy-(3α-THP-ether)-2β-[(3S)-3-hydroxy-(3-THP-ether)-4,4'-difluoro-5-cyclohexyl-trans-1-pentenyl]-1α-cyclopentyl}-ethanal-γ-lactol;
one obtains the following compounds:
18,19,20-trinor-17-cyclohexyl-16S-fluoro-$PGF_{2\alpha}$-11,15-bis-THP-ether;
18,19,20-trinor-17-cyclohexyl-16R-fluoro-$PGF_{2\alpha}$-11,15-bis-THP-ether;
18,19,20-trinor-17-cyclopentyl-16(R,S)-fluoro-$PGF_{2\alpha}$-11,15-bis-THP-ether;
18,19,20-trinor-17-cyclopentyl-16,16-difluoro-$PGF_{2\alpha}$-11,15-bis-THP-ether;
18,19,20-trinor-17-cyclohexyl-16,16-difluoro-$PGF_{2\alpha}$-11,15-bis-THP-ether.

EXAMPLE 2

To a solution of the ylide prepared as described in example 1, starting with 612 mg of NaH (80% dispersion in mineral oil) and 4.52 g of triphenyl-(4-carboxybutyl)-phosphonium bromide, in 25 ml of anhydrous DMSO add a solution of 934 mg of 2-{3α,5α-dihydroxy-(3-THP-ether)-2β-[2-bromo-(3S)-3-hydroxy-(3-THP-ether)-4(R,S)-fluoro-trans-1-nonenyl]-1α-cyclopentyl}-ethanal-γ-lactol in 8 ml of DMSO. Keep at room temperature for 10 hours, then dilute with 30 ml of water and extract with ether to remove the triphenylphosphoxide. The combined ether phases are re-extracted with 0.5 N NaOH and then discarded. The combined aqueous alkaline phases are acidified to pH 4.5 and extracted with ethyl ether:pentane 1:1. These organic extracts are combined, washed to neutral with saturated aqueous ammonium sulfate solution, dried over sodium sulfate and evaporated to dryness. The yield is 860 mg of 13,14-dehydro-16(R,S)-fluoro-20-methyl-11,15-bis-THP-ether-$PGF_{2\alpha}$.

EXAMPLE 3

To a solution of 0.5 g of 18,19,20-trinor-17-cyclohexyl-16(R,S)-fluoro-$PGF_{2\alpha}$-11,15-bis-THP-ether in 8 ml of acetone add 10 ml of a 0.25 N aqueous solution of oxalic acid and reflux for 2 hours. Evaporate the excess acetone under vacuum, extract the aqueous phase with ethyl ether. The organic extracts are combined, washed until neutral with a saturated ammonium sulfate solution, dried and evaporated to dryness. The residue is chromatographed on acid-washed silica gel and eluted with methylene chloride-ethyl acetate 8:2, yielding 320 mg of pure 18,19,20-trinor-17-cyclohexyl-16(R,S)-fluoro-$PGF_{2\alpha}$; $[\alpha]_D^{EtOH} = +15.1°$; $[\alpha]_{365°}^{EtOH} = +46.8°$.

The dioxanyl ethers are deacetalated by the same procedure.

EXAMPLE 4

Add a solution in anhydrous DMSO of 1.75 g of potassium ter-butylate, freshly sublimated, to a solution of 3.46 g of triphenyl-(4-carboxybutyl)-phosphonium bromide in 25 ml of DMSO, maintaining at about 15° C., under inert gas, and with constant stirring. To the dark red solution of the ylide which is formed add a solution of 770 mg of 2-{3α,5α-dihydroxy-(3α-DIOX-ether)-2β-[2-bromo-(3S)-hydroxy-(3-DIOX-ether)-4,4'-difluoro-5-phenyl-trans-1-pentenyl]-1α-cyclopentyl}-ethanal-γ-lactol in 10 ml of a 1:1 mixture of DMSO:THF. Stir for 10 hours, then dilute with 30 ml of water and extracts the aqueous phase with ethyl ether to remove the triphenylphosphoxide. The ether extracts are re-extracted with 0.5 N NaOH and then discarded. The aqueous alkaline phases are combined, acidified to pH 4.5 with 2 N $H_2SO_4$ and extracted with ethyl ether:pentane 1:1. These organic extracts are washed until neutral with saturated ammonium sulfate solution and evaporated to dryness to give 700 mg of 18,19,20-trinor-17-phenyl-16,16-difluoro-13,14-dehydro-$PGF_{2\alpha}$-11,15-bis-DIOX-ether. Following the procedures of example 2 or example 3, starting from the following aldehydes:
2-{3α,5α-dihydroxy-2β-[2-bromo-(3S)-3-hydroxy-4(R,S)-fluoro-trans-1-octenyl]-1α-cyclopentyl}-ethanal-γ-lactol;
2-{3α,5α-dihydroxy-2β-[2-bromo-(3S)-3-hydroxy-4R-fluoro-4S-methyl-trans-1-octenyl]-1α-cyclopentyl}-ethanal-γ-lactol, and its 4R-methyl-4S-fluoro-isomer;
2-{3α,5α-dihydroxy-2β-[2-bromo-(3S)-3-hydroxy-4,4-difluoro-trans-1-octenyl]-1α-cyclopentyl}-ethanal-γ-lactol;
2-{3α,5α-dihydroxy-2β-[2-bromo-(3S)-3-hydroxy-4(R,S)-fluoro-trans-1-nonenyl]-1α-cyclopentyl}-ethanal-γ-lactol;
2-{3α, 5α-dihydroxy-2β-[2-bromo-(3S)-3-hydroxy-4S-fluoro-4R-methyl-trans-1-nonenyl]-1α-cyclopentyl}-ethanal-γ-lactol and its 4S-methyl-4R-fluoro-isomer;
2-{3α,5α-dihydroxy-2β-[2-bromo-(3S)-3-hydroxy-4,4-difluoro-trans-1-nonenyl]-1α-cyclopentenyl}-ethanal-γ-lactol;
2-{3α,5α-dihydroxy-2β-[2-bromo-(3S)-3-hydroxy-4(R,S)-fluoro-trans-1-decenyl]-1α-cyclopentyl}-ethanal-γ-lactol;
2-{3α,5α-dihydroxy-2β-[2-bromo-(3S)-3-hydroxy-4,4-difluoro-trans-1-decenyl]-1α-cyclopentyl}-ethanal-γ-lactol;
2-{3α,5α-dihydroxy-2β-[2-bromo-(3S)-3-hydroxy-4S-fluoro-5-cyclopentyl-trans-1-pentenyl]-1α-cyclopentyl}-ethanal-γ-lactol;
2-{3α,5α-dihydroxy-2β-[2-bromo-(3S)-3-hydroxy-4,4-difluoro-5-cyclopentyl-trans-1-pentenyl]-1α-cyclopentyl}-ethanal-γ-lactol;
2-{3α,5α-dihydroxy-2β-[2-bromo-(3S)-3-hydroxy-4(R,S)-fluoro-5-cyclohexyl-trans-1-pentenyl]-1α- cyclopentyl}-ethanal-γ-lactol and the individual 4S-fluoro and 4R-fluoro isomers;

2-{3α,5α-dihydroxy-2β-[2-bromo-(3S)-3-hydroxy-4,4-difluoro-5-cyclohexyl-trans-1-pentenyl]-1α-cyclopentyl}-ethanal-γ-lactol;

2-{3α,5α-dihydroxy-2β-[2-bromo-(3S)-3-hydroxy-4(R,S)-fluoro-5-phenyl-trans-1-pentenyl]-1α-cyclopentyl}-ethanal-γ-lactol;

2-{3α,5α-dihydroxy-2β-[2-bromo-(3S)-3-hydroxy-4,4-difluoro-5-phenyl-trans-1-pentenyl]-1α-cyclopentyl}-ethanal-γ-lactol;

2-{3α,5α-dihydroxy-2β-[2-bromo-(3S)-3-hydroxy-4(R,S)-fluoro-4-(4'-fluoro)-phenyl-trans-1-pentenyl]-1α-cyclopentyl}-ethanal-γ-lactol;

2-{3α,5α-dihydroxy-2β-[2-bromo-(3S)-3-hydroxy-4(R,S)-fluoro-4-(3'-chloro)-phenyl-trans-1-pentenyl]-1α-cyclopentyl}-ethanal-γ-lactol;

2-{3α,5α-dihydroxy-2β-[2-bromo-(3S)-3-hydroxy-4(R,S)-fluoro-4-(3'-trifluoromethyl)-phenyl-trans-1-pentenyl]-1α-cyclopentyl}-ethanal-γ-lactol, the following compounds are obtained, either as the 11,15-bis-THP-ether or as the 11,15-bis-DIOX-ethers:

13,14-dehydro-16(R,S)-fluoro-PGF$_{2\alpha}$;
13,14-dehydro-16S-methyl-16R-fluoro-PGF$_{2\alpha}$ and its 16S-fluoro-16R-methyl-isomer;
13,14-dehydro-16,16-difluoro-PGF$_{2\alpha}$;
13,14-dehydro-16,16-difluoro-20-methyl-PGF$_{2\alpha}$;
13,14-dehydro-16S-fluoro-16R,20-dimethyl-PGF$_{2\alpha}$ and its 16R-fluoro-16S-methyl-isomer;
13,14-dehydro-16(R,S)-fluoro-20-methyl-PGF$_{2\alpha}$;
13,14-dehydro-16(R,S)-fluoro-20-ethyl-PGF$_{2\alpha}$;
13,14-dehydro-16,16-difluoro-20-ethyl-PGF$_{2\alpha}$;
18,19,20-trinor-17-cyclopentyl-16S-fluoro-13,14-dehydro-PGF$_{2\alpha}$;
18,19,20-trinor-17-cyclopentyl-16,16-difluoro-13,14-dehydro-PGF$_{2\alpha}$;
18,19,20-trinor-17-cyclohexyl-16(R,S)-fluoro-13,14-dehydro-PGF$_{2\alpha}$ and the individual 16S-fluoro and 16R-fluoro isomers;
18,19,20-trinor-17-cyclohexyl-16,16-difluoro-13,14-dehydro-PGF$_{2\alpha}$;
18,19,20-trinor-17-phenyl-16(R,S)-fluoro-13,14-dehydro-PGF$_{2\alpha}$;
18,19,20-trinor-17-phenyl-16,16-difluoro-13,14-dehydro-PGF$_{2\alpha}$;
18,19,20-trinor-16(R,S)-fluoro-17-(4'-fluoro)-phenyl-13,14-dehydro-PGF$_{2\alpha}$;
18,19,20-trinor-16(R,S)-fluoro-17-(3'-chloro)-phenyl-13,14-dehydro-PGF$_{2\alpha}$;
18,19,20-trinor-16(R,S)-fluoro-16-(3'-trifluoromethyl)-phenyl-13,14-dehydro-PGF$_{2\alpha}$; which are then deacetalated by the procedure described in example 3 to give the following free hydroxy acids:

13,14-dehydro-16(R,S)-fluoro-PGF$_{2\alpha}$;
13,14-dehydro-16S-methyl-16R-fluoro-PGF$_{2\alpha}$ and its 16S-fluoro-16R-methyl-isomer;
13,14-dehydro-16,16-difluoro-PGF$_{2\alpha}$;
13,14-dehydro-16,16-difluoro-20-methyl-PGF$_{2\alpha}$;
13,14-dehydro-16S-fluoro-16R,20-dimethyl-PGF$_{2\alpha}$ and its 16R-fluoro-16S-methyl-isomer;
13,14-dehydro-16(R,S)-fluoro-20-methyl-PGF$_{2\alpha}$;
13,14-dehydro-16(R,S)-fluoro-20-ethyl-PGF$_{2\alpha}$;
13,14-dehydro-16,16-difluoro-20-ethyl-PGF$_{2\alpha}$;
18,19,20-trinor-17-cyclopentyl-16S-fluoro-13,14-dehydro-PGF$_{2\alpha}$;
18,19,20-trinor-17-cyclopentyl-16,16-difluoro-13,14-dehydro-PGF$_{2\alpha}$;
18,19,20-trinor-17-cyclohexyl-16(R,S)-fluoro-13,14-dehydro-PGF$_{2\alpha}$ and the individual 16S-fluoro and 16R-fluoro isomers;
18,19,20-trinor-17-cyclohexyl-16,16-difluoro-13,14-dehydro-PGF$_{2\alpha}$;
18,19,20-trinor-17-phenyl-16(R,S)-fluoro-13,14-dehydro-PGF$_{2\alpha}$;
18,19,20-trinor-17-phenyl-16,16-difluoro-13,14-dehydro-PGF$_{2\alpha}$;
18,19,20-trinor-16(R,S)-fluoro-17-(4'-fluoro)-phenyl-13,14-dehydro-PGF$_{2\alpha}$;
18,19,20-trinor-16(R,S)-fluoro-17-(3'-chloro)-phenyl-13,14-dehydro-PGF$_{2\alpha}$;
18,19,20-trinor-16(R,S)-fluoro-16-(3'-trifluoromethyl)-phenyl-13,14-dehydro-PGF$_{2\alpha}$.

EXAMPLE 5

A solution of 0.37 g of 18,19,20-trinor-17-cyclohexyl-16(R,S)-fluoro-PGF$_{2\alpha}$-11,15-bis-THP-ether in 10 ml of acetone is cooled to $-15°$ C. and 0.9 ml of Jones reagent is added. This is maintained at $-10°$ to $-12°$ C. for 30 minutes, then diluted with 70 ml of benzene, washed repeatedly with saturated aqueous ammonium sulfate until neutral (10 times 5 ml). It is then dried over sodium sulfate and evaporated to dryness.

The crude reaction product is dissolved in 60 ml of acetone and combined with 80 ml of an aqueous 0.1 N sodium oxalate solution. The mixture is maintained at 40° C. for 10 hours. The acetone is evaporated under vacuum and the aqueous phase extracted with ether. The combined organic extracts are washed until neutral, dried and evaporated to dryness. The residue is chromatographed on acid-washed silica gel and eluted with methylene chloride-ethyl acetate to give 0.2 g of 18,19,20-trinor-17-cyclohexyl-16(R,S)-fluoro-PGE$_2$, $[\alpha]_D = -47.8°$, $[\alpha]_{365°} = -291°$ (EtOH).

Using the above procedure and starting with compounds prepared as described in examples 1, 2 and 3, in the form of the 11,15-bis-acetals, after oxidation with Jones reagent and subsequent deacetalation the following PGE$_2$ derivatives are obtained:

18,19,20-trinor-17-cyclopentyl-16(R,S)-fluoro-PGE$_2$;
18,19,20-trinor-17-cyclopentyl-16,16-difluoro-PGE$_2$;
18,19,20-trinor-17-cyclohexyl-16(R,S)-PGE$_2$ and the individual 16S and 16R isomers;
18,19,20-trinor-17-cyclohexyl-16,16-difluoro-PGE$_2$;
13,14-dehydro-16(R,S)-fluoro-PGE$_2$;   $[\alpha]_D = -3.6°$ (EtOH);
13,14-dehydro-16S-methyl-16R-fluoro-PGE$_2$ and its 16R-methyl-16S-fluoro-isomer;
13,14-dehydro-16,16-difluoro-PGE$_2$;
13,14-dehydro-16(R,S)-fluoro-20-methyl-PGE$_2$;
13,14-dehydro-16S-fluoro-16R,20—dimethyl-PGE$_2$ and its 16S-methyl-16R-fluoro-isomer;
13,14-dehydro-16,16-difluoro-20-methyl-PGE$_2$;
13,14-dehydro-16(R,S)-fluoro-20-ethyl-PGE$_2$;
13,14-dehydro-16,16-difluoro-20-ethyl-PGE$_2$;
18,19,20-trinor-17-cyclopentyl-16(R,S)-fluoro-13,14-dehydro-PGE$_2$;
18,19,20-trinor-17-cyclopentyl-16,16-difluoro-13,14-dehydro-PGE$_2$;
18,19,20-trinor-17-cyclohexyl-16(R,S)-fluoro-13,14-dehydro-PGE$_2$ and the individual 16S-fluoro and 16R-fluoro isomers;
18,19,20-trinor-17-cyclohexyl-16,16-difluoro-13,14-dehydro-PGE$_2$;
18,19,20-trinor-17-phenyl-16(R,S)-fluoro-13,14-dehydro-PGE$_2$;

18,19,20-trinor-17-phenyl-16,16-difluoro-13,14-dehydro-PGE$_2$;
18,19,20-trinor-16(R,S)-fluoro-17-(4'-fluoro)-phenyl-13,14-dehydro-PGE$_2$;
18,19,20-trinor-16(R,S)-fluoro-16-(3'-chloro)-phenyl-13,14-dehydro-PGE$_2$.

EXAMPLE 6

A solution of 0.59 g of 18,19,20-trinor-17-cyclohexyl-16(R,S)-fluoro-PGE$_2$-11,15-bis-THP-ether in 80 ml of acetone is refluxed with 50 ml of an aqueous 0.25 N solution of oxalic acid for 6 hours. The acetone is evaporated under vacuum and the residue extracted repeatedly with ethyl ether. The combined ether extracts are washed with saturated aqueous ammonium sulfate and dried down. The residue is chromatographed on acid-washed silica gel, eluted with cyclohexane-ethyl acetate 80:20, yielding 300 mg of 18,19,20-trinor-17-cyclohexyl-16(R,S)-fluoro-PGA$_2$.

Using the above procedure and starting with compounds prepared as outlined in example 5, either in the form of the free alcohols or of the 11,15-bis-THP-ethers or 11,15-bis-DIOX-ethers, one prepares the following compounds:
18,19,20-trinor-17-cyclopentyl-16(R,S)-fluoro-PGA$_2$;
18,19,20-trinor-17-cyclohexyl-16(R,S)-fluoro-PGA$_2$;
13,14-dehydro-16(R,S)-fluoro-PGA$_2$;
13,14-dehydro-16S-methyl-16R-fluoro-PGA$_2$;
13,14-dehydro-16,16-difluoro-PGA$_2$;
13,14-dehydro-16(R,S)-fluoro-20-methyl-PGA$_2$;
13,14-dehydro-16S-fluoro-16R,20-dimethyl-PGA$_2$;
13,14-dehydro-16,16-difluoro-20-methyl-PGA$_2$;
13,14-dehydro-16(R,S)-fluoro-20-ethyl-PGA$_2$;
13,14-dehydro-16,16-difluoro-20-ethyl-PGA$_2$;
18,19,20-trinor-17-cyclopentyl-16(R,S)-fluoro-13,14-dehydro-PGA$_2$;
18,19,20-trinor-17-cyclopentyl-16,16-difluoro-13,14-dehydro-PGA$_2$;
18,19,20-trinor-17-cyclohexyl-16S-fluoro-13,14-dehydro-PGA$_2$ and its 16R isomer;
18,19,20-trinor-17-cyclohexyl-16,16-difluoro-13,14-dehydro-PGA$_2$;
18,19,20-trinor-17-phenyl-16(R,S)-fluoro-13,14-dehydro-PGA$_2$;
18,19,20-trinor-17-phenyl-16,16-difluoro-13,14-dehydro-PGA$_2$.

EXAMPLE 7

To a solution of 0.58 g of 18,19,20-trinor-17-cyclohexyl-16(R,S)-fluoro-PGF$_{2\alpha}$-11,15-bis-THP-ether in 12 ml of HMPA are added 44 mg of NaOH dissolved in 1 ml of water. This is stirred for 1 hour. Then add 150 mg of 1-bromo-propane and continue to stir for 12 hours. Then add 25 ml of water and extract with ethyl ether. The combined organic phases are washed with saturated aqueous ammonium sulfate, dried and evaporated to dryness to give 600 mg of 18,19,20-trinor-17-cyclohexyl-16(R,S)-fluoro-PGF$_{2\alpha}$-11,15-bis-THP-ether-n-propylester.

By this procedure, starting with the 11,15-bis-acetalic ethers described in examples 1, 2 and 3 and using instead of the 1-bromo-propane another haloalkyl compound (for instance methyl iodide, ethyl iodide, bromo-butane, bromo-octane, bromo-decane) one can prepare the methyl, ethyl, butyl, octyl or decyl esters of the corresponding 11,15-bis-acetalic ethers, that can then be deacetalated by the procedure of example 3 to give the free hydroxy esters.

EXAMPLE 8

To a solution of 0.6 g of 18,19,20-trinor-17-cyclohexyl-16(R,S)-fluoro-PGF$_{2\alpha}$-11,15-bis-THP-ether-n-propyl ester in 15 ml of anhydrous THF are added 1.05 g of triphenyl phosphine and 0.79 g of p-phenylbenzoic acid. The reaction mixture is maintained at 20°–22° C. and stirred while a solution of 0.7 g of ethyl azadicarboxylate in 6 ml of THF is added drop by drop over a five minute period. After an additional 10 minutes, evaporate to dryness and take up the residue in 75 ml of ethyl ether, wash with a saturated aqueous solution of bicarbonate, then water and evaporate to dryness. The residue is dissolved in 25 ml of acetone and 18 ml of 0.2 N aqueous oxalic acid solution are added. The mixture is refluxed for 30 minutes, concentrated under vacuum to remove the acetone, extracted with ethyl acetate and the organic phase is evaporated to dryness. The residue is chromatographed on silica gel, eluted first with cyclohexane-ethyl ether 6:4 and then with ethyl ether to give 0.5 g of 18,19,20-trinor-17-cyclohexyl-16(R,S)-fluoro-PGF$_{2\beta}$-9-p-phenylbenzoate-n-propylester. A solution of this compound in 10 ml of anhydrous propanol is treated with 140 mg of anhydrous potassium carbonate and the mixture is refluxed for an hour and 30 minutes. It is then neutralized, the solvent is evaporated off and the reaction partitioned between methylene chloride and water. The organic phase is dried and evaporated to dryness and the residue is chromatographed on silica gel, first eluted with ethyl ether and then with ethyl ether-ethyl acetate 1:1. The yield is 340 mg of 18,19,20-trinor-17-cyclohexyl-16(R,S)-fluoro-PGF$_{2\beta}$-n-propyl ester. This compound is dissolved in a 8:2 mixture of methanol-water and 215 mg of potassium carbonate are added.

Reflux for one hour. After evaporation of the solvent, take up in water, acidify to pH 4.5 and extract with ethyl acetate. After evaporation of the organic phase, one obtains 280 mg of 18,19,20-trinor-17-cyclohexyl-16-(R,S)-fluoro-PGF$_{2\beta}$. Using the procedures of examples 7 and 8, starting with compounds prepared as described in examples 1, 2 and 3, the following compounds are prepared as free acids or as alkyl esters:
18,19,20-trinor-17-cyclopentyl-16(R,S)-fluoro-PGF$_{2\beta}$;
18,19,20-trinor-17-cyclopentyl-16,16-difluoro-PFG$_{2\beta}$;
18,19,20-trinor-17-cyclohexyl-16(R,S)-fluoro-PGF$_{2\beta}$;
18,19,20-trinor-17-cyclohexyl-16,16-difluoro-PGF$_{2\beta}$;
13,14-dehydro-16(R,S)-fluoro-PFG$_{2\beta}$;
13,14-dehydro-16S-methyl-16R-fluoro-PGF$_{2\beta}$ and its 16R-methyl-16S-fluoro isomer;
13,14-dehydro-16,16-difluoro-PGF$_{2\beta}$;
13,14-dehydro-16(R,S)-fluoro-20-methyl-PGF$_{2\beta}$;
13,14-dehydro-16S-fluoro-16R,20-dimethyl-PGF$_{2\beta}$ and its 16S-methyl-16R-fluoro-isomer;
13,14-dehydro-16,16-difluoro-20-methyl-PGF$_{2\beta}$;
13,14-dehydro-16(R,S)-fluoro-20-ethyl-PGF$_{2\beta}$;
13,14-dehydro-16,16-difluoro-20-ethyl-PGF$_{2\beta}$;
18,19,20-trinor-17-cyclopentyl-16(R,S)-fluoro-13,14-dehydro-PGF$_{2\beta}$;
18,19,20-trinor-17-cyclopentyl-16,16-difluoro-13,14-dehydro-PGF$_{2\beta}$;
18,19,20-trinor-17-cyclohexyl-16(R,S)-fluoro-13,14-dehydro-PGF$_{2\beta}$;
18,19,20-trinor-17-phenyl-16(R,S)-fluoro-13,14-dehydro-PGF$_{2\beta}$.

EXAMPLE 9

With humidity excluded, under an atmosphere of inert gas, and with constant stirring, add drop by drop to a suspension of 410 mg of NaH (80% dispersion in mineral oil) in 100 ml of anhydrous benzene a solution of 3.82 g of dimethoxy-[2-oxo-3-fluoro-4-cyclohexyl]-butyl phosphonate in 10 ml of anhydrous benzene. Stir for one hour and then add all at once a solution of 2 g of 2-{[2β-formyl-3α,5α-dihydroxy-(3α-p-phenylbenzoate)]-1α-cyclopentyl}-acetic acid-1,5-γ-lactone in anhydrous benzene. Stir for 15 minutes and then add 100 ml of a saturated aqueous solution of monobasic sodium phosphate, separate the organic phase, wash it until neutral, dry and evaporate to dryness. The residue is chromatographed on silica gel and eluted with cyclohexane-ethylacetate 8:2 to give 2.1 g of 2-{3α,5α-dihydroxy-(3α-p-phenylbenzoate)-2β-[3-keto-4-fluoro-5-cyclohexyl-trans-1-pentenyl]-1α-cyclopentyl}-acetic acid-1,5-γ-lactone, m.p. 127°–129° C.

EXAMPLE 10

Add drop by drop to a suspension of 410 mg of NaH (80% dispersion in mineral oil) in 140 ml of anhydrous THF a solution of 3.82 g of dimethyl-[2-oxo-3(R,S)-fluoro-cyclohexyl]-butyl-phosphonate in 10 ml of THF. Stir one hour until no more hydrogen evolves. Then add all at once 2.432 g of N-bromo-succinimide. Stir for 15 minutes and then add a solution in THF of 2 g of 2-{[2β-formyl-3α,5α-dihydroxy-(3α-p-phenylbenzoate)]-1α-cyclopentyl}-acetic acid-1,5-γ-lactone. The mixture is stirred for one hour and then diluted with 200 ml of a 6% aqueous solution of monobasic sodium phosphate. The organic phase is separated, washed until neutral, dried and evaporated to dryness. After chromatography on a silica gel column, 1.9 g are obtained of 2-{3α,5α-dihydroxy-(3α-p-phenylbenzoate)-2β-[2-bromo-3-keto-4(R,S)-fluoro-5-cyclohexyl-trans-1-pentenyl]-1α-cyclopentyl}-acetic acid-1,5-γ-lactone.

Following the procedures of examples 9 and 10, we obtained the following acid-1,5-γ-lactones: 2-{3α,5α-dihydroxy-(3α-p-phenylbenzoate)-2β-[3-keto-4(R,S)-fluoro-5-cyclopentyl-trans-1-pentenyl]-1α-cyclopentyl}-acetic acid-1,5-γ-lactone;

2-{3α,5α-dihydroxy-(3α-p-phenylbenzoate)-2β-[3-keto-4,4-difluoro-5-cyclopentyl-trans-1-pentenyl]-1α-cyclopentyl}-acetic acid-1,5-γ-lactone;

2-{3α,5α-dihydroxy-(3α-p-phenylbenzoate)-2β-[3-keto-4(R,S)-fluoro-5-cyclohexyl-trans-1-pentenyl]-1α-cyclopentyl}-acetic acid-1,5-γ-lactone;

2-{3α,5α-dihydroxy-(3α-p-phenylbenzoate)-2β-[3-keto-4,4-difluoro-5-cyclohexyl-trans-1-pentenyl]-1α-cyclopentyl}-acetic acid-1,5-γ-lactone;

2-{3α,5α-dihydroxy-(3α-p-phenylbenzoate)-2β-[2-bromo-3-keto-4(R,S)-fluoro-trans-1-octenyl]-1α-cyclopentyl}-acetic acid-1,5-γ-lactone;

2-{3α,5α-dihydroxy-(3α-p-phenylbenzoate)-2β-[2-bromo-3-keto-4,4-difluoro-trans-1-octenyl]-1α-cyclopentyl}-acetic acid-1,5-γ-lactone;

2-{3α,5α-dihydroxy-(3α-p-phenylbenzoate)-2β-[2-bromo-3-keto-4S-methyl-4R-fluoro-trans-1-octenyl]-1α-cyclopentyl}-acetic acid-1,5-γ-lactone and its 4R-methyl-4S-fluoro isomer;

2-{3α,5α-dihydroxy-(3α-p-phenylbenzoate)-2β-[2-bromo-3-keto-4(R,S)-fluoro-trans-1-nonenyl]-1α-cyclopentyl}-acetic acid-1,5-γ-lactone;

2-{3α,5α-dihydroxy-(3α-p-phenylbenzoate)-2β-[2-bromo-3-keto-4S-fluoro-4R-methyl-trans-1-nonenyl]-1α-cyclopentyl}-acetic acid-1,5-γ-lactone and its 4S-methyl-4R-fluoro isomer;

2-{3α,5α-dihydroxy-(3α-p-phenylbenzoate)-2β-[2-bromo-3-keto-4,4-difluoro-trans-1-nonenyl]-1α-cyclopentyl}-acetic acid-1,5-γ-lactone;

2-{3α,5α-dihydroxy-(3α-p-phenylbenzoate)-2β-[2-bromo-3-keto-4(R,S)-fluoro-trans-1-decenyl]-1α-cyclopentyl}-acetic acid-1,5-γ-lactone; 2-{3α,5α-dihydroxy-(3α-p-phenylbenzoate)-2β-[2-bromo-3-keto-4,4-difluoro-trans-1-decenyl]-1α-cyclopentyl}-acetic acid-1,5-γ-lactone;

2-{3α,5α-dihydroxy-(3α-p-phenylbenzoate)-2β-[2-bromo-3-keto-4(R,S)-fluoro-5-cyclopentyl-trans-1-pentenyl]-1α-cyclopentyl}-acetic acid-1,5-γ-lactone;

2-{3α,5α-dihydroxy-(3α-p-phenylbenzoate)-2β-[2-bromo-3-keto-4,4-difluoro-5-cyclopentyl-trans-1-pentenyl]-1α-cyclopentyl}-acetic acid-1,5-γ-lactone;

2-{3α,5α-dihydroxy-(3α-p-phenylbenzoate)-2β-[2-bromo-3-keto-4(R,S)-fluoro-cyclohexyl-trans-1-pentenyl]-1α-cyclopentyl}-acetic acid-1,5-γ-lactone and the individual 4R and 4S isomers;

2-{3α,5α-dihydroxy-(3α-p-phenylbenzoate)-2β-[2-bromo-3-keto-4,4-difluoro-5-cyclohexyl-trans-1-pentenyl]-1α-cyclopentyl}-acetic acid-1,5-γ-lactone;

2-{3α,5α-dihydroxy-(3α-p-phenylbenzoate)-2β-[2-bromo-3-keto-4(R,S)-fluoro-5-phenyl-trans-1-pentenyl]-1α-cyclopentyl}-acetic acid-1,5-γ-lactone;

2-{3α,5α-dihydroxy-(3α-p-phenylbenzoate)-2β-[2-bromo-3-keto-4,4-difluoro-5-phenyl-trans-1-pentenyl]-1α-cyclopentyl}-acetic acid-1,5-γ-lactone;

2-{3α,5α-dihydroxy-(3α-p-phenylbenzoate)-2β-[2-bromo-3-keto-4(R,S)-fluoro-5-(4'-fluoro)-phenyl-trans-1-pentenyl]-1α-cyclopentyl}-acetic acid-1,5-γ-lactone;

2-{3α,5α-dihydroxy-(3α-p-phenylbenzoate)-2β-[2-bromo-3-keto-4(R,S)-fluoro-5-(3'-chloro)-phenyl-trans-1-pentenyl]-1α-cyclopentyl}-acetic acid-1,5-γ-lactone;

2-{3α,5α-dihydroxy-(3α-p-phenylbenzoate)-2β-[2-bromo-3-keto-4(R,S)-fluoro-5-(3'-trifluoromethyl)-phenyl-trans-1-pentenyl]-1α-cyclopentyl}-acetic acid-1,5-γ-lactone.

EXAMPLE 11

Dissolve 2.03 g of 2-{3α,5α-dihydroxy-(3α-p-phenylbenzoate)-2β-[3-keto-4(R,S)-fluoro-5-cyclohexyl-trans-1-pentenyl]-1α-cyclopentyl}-acetic acid-1,5-γ-lactone in 120 ml of a 5:1 mixture of anhydrous ethyl ether:DME and add drop by drop, with stirring, 280 ml of a 0.07 M solution of Zn(BH$_4$)$_2$ in ethyl ether, at room temperature. Stir for 30 minutes and then add 40 ml of a saturated aqueous sodium chloride solution and then 55 ml of 2N H$_2$SO$_4$. Separate off the organic phase and wash to neutral, then dry and evaporate to dryness. The residue is chromatographed on a silica gel column eluted with methylene chloride-ether 9:1. One obtains 1.18 g of 2-{3α,5α-dihydroxy-(3α-p-phenylbenzoate)-2β-[(3S)-3-hydroxy-4(R,S)-fluoro-5-cyclohexyl-trans-1-pentenyl]-1α-cyclopentyl}-acetic acid-1,5-γ-lactone and 780 mg of 2-{3α,5α-dihydroxy-(3α-p-phenylbenzoate)-2β-[(3R)-3-hydroxy-4(R,S)-fluoro-5-cyclohexyl-trans-1-pentenyl]-1α-cyclopentyl}-acetic acid-1,5-γ-lactone, m.p. 116°–118° C., [α]$_D$= −105° (CHCl$_3$).

EXAMPLE 12

Dissolve 1.18 g of 2-{3α,5α-dihydroxy-(3α-p-phenylbenzoate)-2β-[(3S)-3-hydroxy-4(R,S)-fluoro-5-cyclohexyl-trans-1-pentenyl]-1α-cyclopentyl}-acetic acid-1,5-γ-lactone in 60 ml of anhydrous methanol. Add 360 mg of anhydrous K$_2$CO$_3$ and stir for 4 hours. Dilute with a saturated solution of monobasic sodium phosphate and filter. The filtrate is concentrated to a small volume, taken up in water and extracted with ethyl acetate. The combined organic phases are washed to neutral, dried and evaporated to dryness. The residue is chromatographed on silica gel, eluted with a mixture of cyclohexane-ethyl acetate.

One obtains 750 mg of 2-{3α,5α-dihydroxy-2β-[(3S)-3-hydroxy-4(R,S)-fluoro-5-cyclohexyl-trans-1-pentenyl]-1α-cyclopentyl}-acetic acid-1,5-γ-lactone.

EXAMPLE 13

Dissolve 370 mg of 2-{3α,5α-dihydroxy-2β-[(3S)-3-hydroxy-4(R,S)-fluoro-5-cyclohexyl-trans-1-pentenyl]-1α-cyclopentyl}-acetic acid-1,5-γ-lactone in 50 ml of anhydrous benzene.

Add 2 mg of p-toluenesulfonic acid and 0.3 ml of 1,2-dihydropyran. Let stand at room temperature for 4 hours, then wash with 3% aqueous potassium carbonate and with water until neutral. Dry and evaporate. One obtains 560 mg of 2-{3α,5α-dihydroxy-(3α-THP-ether)-2β-[(3S)-3-hydroxy-(3-THP-ether)-4(R,S)-fluoro-5-cyclohexyl-trans-1-pentenyl]-1α-cyclopentyl}-acetic acid-1,5-γ-lactone.

EXAMPLE 14

Dissolve 460 mg of 2-{3α,5α-dihydroxy-(3α-THP-ether)-2β-(3S)-3-hydroxy-(3-THP-ether)-4(R,S)-fluoro-5-cyclohexyl-trans-1-pentenyl]-1α-cyclopentyl}-acetic acid-1,5-γ-lactone in 20 ml of anhydrous toluene. This solution is cooled to −70° C. and maintained at temperatures not higher than −60° C. while adding drop by drop a solution of 7.21% DIBA in toluene. After it has all been added, stir for an additional 30 minutes. Then add 3.2 ml of 2 M isopropanol in anhydrous toluene, let the temperature rise to 0° C. and add 2 ml of water. Continue to stir for about 20 minutes and then add 500 mg of celite and 1.0 g of anhydrous sodium sulfate. Filter and evaporate the filtrate to give 400 mg of 2-{3α,5α-dihydroxy-(3-THP-ether)-2β-[(3S)-3-hydroxy-(3-THP-ether)-4(R,S)-fluoro-5-cyclohexyl-trans-1-pentenyl]-1α-cyclopentyl}-ethanal-1,5-γ-lactol.

Following the procedures of examples 11 to 13 and starting from compounds prepared according to the procedures of examples 9 and 10, one obtains the following compounds (either as bis-THP-ethers or as bis-DIOX-ethers): 2-{3α,5α-dihydroxy-2β-[(3S)-3-hydroxy-4(R,S)-fluoro-5-cyclopentyl-trans-1-pentenyl]-1α-cyclopentyl}-ethanal-γ-lactol;

2-{3α,5α-dihydroxy-2β-[(3S)-3-hydroxy-4,4-difluoro-5-cyclopentyl-trans-1-pentenyl]-1α-cyclopentyl}-ethanal-γ-lactol;

2-{3α,5α-dihydroxy-2β-[(3S)-3-hydroxy-4(R,S)-fluoro-5-cyclohexyl-trans-1-pentenyl]-1α-cyclopentyl}-ethanal-γ-lactol and the individual 4S and 4R isomers;

2-{3α,5α-dihydroxy-2β-[(3S)-3-hydroxy-4,4-difluoro-5-cyclohexyl-trans-1-pentenyl]-1α-cyclopentyl}-ethanal-γ-lactol;

2-{3α,5α-dihydroxy-2β-[2-bromo-(3S)-3-hydroxy-4(R,S)-fluoro-trans-1-octenyl]-1α-cyclopentyl}-ethanal-γ-lactol;

2-{3α,5α-dihydroxy-2β-[2-bromo-(3S)-3-hydroxy-4S-methyl-4R-fluoro-trans-1-octenyl]-1α-cyclopentyl}-ethanal-γ-lactol and the 4S-fluoro-4R-methyl isomer;

2-{3α,5α-dihydroxy-2β-[2-bromo-(3S)-3-hydroxy-4,4-difluoro-trans-1-octenyl]-1α-cyclopentyl}-ethanal-γ-lactol;

2-{3α,5α-dihydroxy-2β-[2-bromo-(3S)-3-hydroxy-4(R,S)-fluoro-trans-1-nonenyl]-1α-cyclopentyl}-ethanal-γ-lactol;

2-{3α,5α-dihydroxy-2β-[2-bromo-(3S)-3-hydroxy-4S-fluoro-4R-methyl-trans-1-nonenyl]-1α-cyclopentyl}-ethanal-γ-lactol and the 4S-methyl-4R-fluoro isomer;

2-{3α,5α-dihydroxy-2β-[2-bromo-(3S)-3-hydroxy-4,4-difluoro-trans-1-nonenyl]-1α-cyclopentyl}-ethanal-γ-lactol;

2-{3α,5α-dihydroxy-2β-[2-bromo-(3S)-3-hydroxy-4(R,S)-fluoro-trans-1-decenyl]-1α-cyclopentyl}-ethanal-γ-lactol;

2-{3α,5α-dihydroxy-2β-[2-bromo-(3S)-3-hydroxy-4,4-difluoro-trans-1-decenyl]-1α-cyclopentyl}-ethanal-γ-lactol;

2-{3α,5α-dihydroxy-2β-[2-bromo-(3S)-3-hydroxy-4(R,S)-fluoro-5-cyclopentyl-trans-1-pentenyl]-1α-cyclopentyl}-ethanal-γ-lactol;

2-{3α,5α-dihydroxy-2β-[2-bromo-(3S)-3-hydroxy-4,4-difluoro-5-cyclopentyl-trans-1-pentenyl]-1α-cyclopentyl}-ethanal-γ-lactol;

2-{3α,5α-dihydroxy-2β-[2-bromo-(3S)-3-hydroxy-4(R,S)-fluoro-5-cyclohexyl-trans-1-pentenyl]-1α-cyclopentyl}-ethanal-γ-lactol and the individual 4S and 4R isomers;

2-{3α,5α-dihydroxy-2β-[2-bromo-(3S)-3-hydroxy-4,4-difluoro-5-cyclohexyl-trans-1-pentenyl]-1α-cyclopentyl}-ethanal-γ-lactol;

2-{3α,5α-dihydroxy-2β-[2-bromo-(3S)-3-hydroxy-4(R,S)-fluoro-5-phenyl-trans-1-pentenyl]-1α-cyclopentyl}-ethanal-γ-lactol;

2-{3α,5α-dihydroxy-2β-[2-bromo-(3S)-3-hydroxy-4,4-difluoro-5-phenyl-trans-1-pentenyl]-1α-cyclopentyl}-ethanal-γ-lactol;

2-{3α,5α-dihydroxy-2β-[2-bromo-(3S)-3-hydroxy-4(R,S)-fluoro-5-(4'-fluoro)-phenyl-trans-1-pentenyl]-1α-cyclopentyl}-ethanal-γ-lactol;

2-{3α,5α-dihydroxy-2β-[2-bromo-(3S)-3-hydroxy-4(R,S)-fluoro-5-(3'-chloro)-phenyl-trans-1-pentenyl]-1α-cyclopentyl}-ethanal-γ-lactol;

2-{3α,5α-dihydroxy-2β-[2-bromo-(3S)-3-hydroxy-4(R,S)-fluoro-5-(3'-trifluoromethyl)-phenyl-trans-1-pentenyl]-1α-cyclopentyl}-ethanal-γ-lactol.

These compounds can be deacetalated as shown in the following example (whether they are bis-THP-ethers or bis-DIOX-ethers).

EXAMPLE 15

0.5 g of 2-{3α,5α-dihydroxy-(3α-THP-ether)-2β-(3S)-3-hydroxy-(3-THP-ether)-4(R,S)-fluoro-5-cyclohexyl-trans-1-pentenyl]-1α-cyclopentyl}-ethanal-γ-lactol in 10 ml of acetone is treated with 5 ml of 0.25 N aqueous oxalic acid and refluxed for 90 minutes. The solvent is evaporated off under vacuum and the aqueous phase is extracted with ethyl acetate. The combined organic extracts are washed with saturated aqueous ammonium sulfate, dried and evaporated to dryness. The residue is chromatographed on silica gel and eluted with ethyl acetate. to give 320 mg of 2-{3α,5α-dihydroxy-2β-[(3S)-3-hydroxy-4(R,S)-fluoro-5-cyclohexyl-trans-1-pentenyl]-1α-cyclopentyl}-ethanal-γ-lactol.

EXAMPLE 16

0.78 g of 2-{3α,5α-dihydroxy-(3α-p-phenylbenzoate)-2β-[(3R)-3-hydroxy-4S-fluoro-5-cyclohexyl-trans-1- pentenyl]-1α-cyclopentyl}-acetic acid-1,5-γ-lactone in 25 ml of anhydrous methanol is reacted for two hours at room temperature with 150 mg of anhydrous K₂CO₃.lt is then neutralized and treated with amberlite 1R 120 resin (H⁺), filtered and the filtrate evaporated to dryness. The residue is taken up in 10 ml of dichloroethane and treated with 0.8 ml of 2,3-dihydropyran and 4 mg of p-toluenesulfonic acid. After 2 hours at room temperature, add 0.3 ml of pyridine and evaporate to dryness to give 0.9 g of 2-{3α,5α-dihydroxy-(3α-THP-ether)-2β-[(3R)-3-hydroxy-(3-THP-ether)-4S-fluoro-5-cyclohexyl-trans-1-pentenyl]-1α-cyclopentyl}-acetic acid-1,5-γ-lactone. This is dissolved in 10 ml of toluene, cooled to −60° C., and under an atmosphere of nitrogen is treated with 6.5 ml of DIBA (0.5 M in toluene). After 30 minutes at −60° C., destroy the excess reagent with 7 ml of a 2 M solution of isopropanol in toluene, to obtain 0.88 g of 2-{3α,5α-dihydroxy-(3α-THP-ether)-2β-[(3R)-3-hydroxy-(3-THP-ether)-4S-fluoro-5-cyclohexyl-trans-1-pentenyl]-1α-cyclopentyl}-ethanal-1,5-γ-lactol. This compound is then reacted by the procedure outlined in example 1 with the ylide generated from 0.92 g of NaH and 6.7 g of triphenyl-(4-carboxy-butyl)-phosphonium bromide in 20 ml of DMSO, giving 0.96 g of 18,19,20-trinor-17-cyclohexyl-16S-fluoro-15-epi-PGF$_{2α}$-11,15-bis-THP-ether. This compound is deacetalated in acetone with aqueous oxalic acid, as described in example 3, to give the 18,19,20-trinor-17-cyclohexyl-16S-fluoro-15-epi-PGF$_{2α}$, $[α]_D = +4.8°$ (EtOH).

In a parallel procedure, by oxidation of the 11,15-bis-tetrahydropyranyl-ether derivative with Jones reagent, according to the procedure of example 5, followed by deacetalation, one obtains 18,19,20-trinor-17-cyclohexyl-16S-fluoro-15-epi-PGE$_2$, $[α]_D = −63.2°$, $[α]_{365°} = −326°$ (EtOH).

EXAMPLE 17

8 ml of 0.2 N oxalic acid are added to a solution of 380 mg of 18,19,20-trinor-17-cyclohexyl-16(S,R)-fluoro-13,14-dehydro-PGF$_{2α}$-11,15-bis-THP-ether, $[α]_D = +9°$, $[α]_{365°} = +102°$ (acetone) in 10 ml of acetone. After 12 hours at 38° C. the acetone is evaporated under vacuum and the residue is ectracted with ethyl ether. The organic extracts are evaporated to dryness and the residue chromatrgraphed on silica gel, eluted with 50:50 methylene chloride:ethyl acetate, to give 120 mg of 18,19,20-trinor-17-cyclohexyl-16(S,R)-fluoro-13,14-dehydro-PGF$_{2α}$, $[α]_D = +38°$ (EtOH).

EXAMPLE 18

0.65 g of 18,19,20-trinor-17-cyclohexyl-16(S,R)-fluoro-13,14-dehydro-PGF$_{2α}$-11,15-bis-THP-ether is dissolved in 20 ml of acetone. The solution is cooled to −15° C. and 1.3 ml of Jones reagent are added. After 15 minutes, dilute with 100 ml of benzene and wash until neutral with 20% ammonium sulfate solution. Dry over sodium sulfate and evaporate to dryness to give 0.52 g of 18,19,20-trinor-17-cyclohexyl-16(S,R)-fluoro-13,14-dehydro-PGE$_2$-11,15-bis-THP-ether, $[α]_D = −23°$ (acetone). This compound is dissolved in 15 ml of acetone, 12 ml of 0.1 N oxalic acid is added, and the mixture allowed to stand for 12 hours at 37° C. The acetone is distilled off under vacuum, the residue is extracted with ethyl acetate and the ethyl acetate extracts evaporated to dryness. The residue (0.39 g) is chromatographed on 12 g of silica gel and eluted with methylene chloride-ethyl acetate (80:20) to obtain 0.2 g of 18,19,20-trinor-17-cyclohexyl-16(S,R)-fluoro-13,14-dehydro-PGE$_2$, $[α]_D = −6.2°$ (EtOH).

We claim:
1. An optically active or racemic compound of the formula:

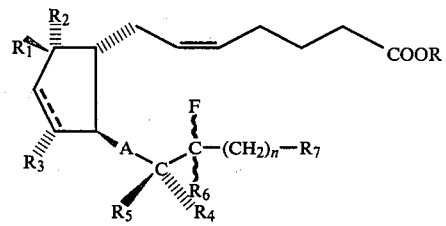

wherein:
R is a member selected from the group consisting of hydrogen, a $C_1$-$C_{12}$ alkyl group and a cation of pharmaceutically acceptable base; the symbol --- represents a single or a double bond, wherein, when the symbol --- is a double bond, $R_3$ is a hydrogen atom and $R_1$ and $R_2$ together form an oxo group, while, when the symbol --- is a single bond, $R_3$ is hydroxy, and one of $R_1$ and $R_2$, is hydrogen and the other is hydroxy or 'alkanoyloxy group containing up to 6 carbon atoms, a benzyloxy or a P-phenylbenzoyloxy group' or $R_1$ and $R_2$, taken together, form an oxo group;
A is —C≡C—;
one of $R_4$ and $R_5$ is hydroxy and the other is hydrogen;
$R_6$ is a member selected from the group consisting of hydrogen, methyl and fluorine;
n is zero, or an integer of 1 to 6;
$R_7$ is cycloalkyl containing 3 to 7 ring carbon atoms.
2. The compound of claim 1 wherein R is methyl.
3. The compound 18,19,20-trinor-17-cyclohexyl 13,14-dehydro-16(S,R)-fluoro-PGF$_{2α}$, the lower alkyl esters or the pharmaceutically acceptable salts thereof.
4. The compound 18,19,20-trinor-17-cyclohexyl-16R-fluoro-13,14-dehydro-PGF$_{2α}$, the methyl ester or the pharmaceutically acceptable salts thereof.
5. The compound 18,19,20-trinor-17-cyclohexyl-16S-fluoro-13,14-dehydro-PGF$_{2α}$, the methyl ester or the pharmaceutically acceptable salts thereof.
6. A compound selected from the group consisting of:
18,19,20-trinor-17-cyclohexyl-16(R,S)-fluoro-13,14-dehydro-PGF$_{2α}$,
18,19,20-trinor-17-cyclohexyl-16R-fluoro-13,14-dehydro-PGF$_{2α}$,
18,19,20-trinor-17-cyclohexyl-16S-fluoro-13,14-dehydro-PGF$_{2α}$,
18,19,20-trinor-17-cyclohexyl-16,16-di-fluoro-13,14-dehydro-PGF$_{2α}$,
a 16-fluoro-18,19,20-trinor-17-cyclopentyl-13,14-dehydro-PGF$_{2α}$,
a 16-fluoro-18,19,20-trinor-17-cyclopentyl-13,14-dehydro-PGE$_2$,
a 16-fluoro-18,19,20-trinor-17-cyclohexyl-13,14-dehydro-PGE$_2$,
18,19,20-trinor-17-cyclopentyl-16,16-difluoro-13,14-dehydro-PGF$_{2α}$,
18,19,20-trinor-17-cyclopentyl-16,16-difluoro-13,14-dehydro-PGE$_2$,
18,19,20-trinor-17-cyclohexyl-16,16-difluoro-13,14-dehydro-PGE$_2$, and the lower alkyl esters and the pharmaceutically acceptable salts thereof.

7. The compound of claim 6 wherein the lower alkyl ester is the methyl ester.

8. A luteolytic, abortive or antiulcer pharmaceutical composition comprising an effective amount of a compound of claim 1 together with a pharmaceutically acceptable carrier or diluent.

9. A method of inducing abortion in a subject in need of said treatment, said method comprising administering to said subject an abortion-inducing amount of a compound of claim 1 wherein $R_2$ and $R_3$ are both hydroxy, or wherein $R_3$ is hydroxy and $R_1$ and $R_2$ together form an oxo group.

10. The method of claim 9, wherein said compound is 18,19,20-trinor-17-cyclohexyl-13,14-dehydro-16(S,R)-fluoro-$PGF_{2\alpha}$, the lower alkyl esters or the pharmaceutically acceptable salts thereof.

11. A method of inducing abortion in a subject comprising administering to said subject an abortion-inducing amount of 18,19,20-trinor-17-cyclohexyl-16R-fluoro-13,14-dehydro-$PGF_{2\alpha}$, the methyl ester or the pharmaceutically acceptable salts thereof.

12. A method of inducing abortion in a subject comprising administering to said subject an abortion-inducing amount of 18,19,20-trinor-17-cyclohexyl-16S-fluoro-13,14-dehydro-$PGF_{2\alpha}$, the methyl ester or the pharmaceutically acceptable salts thereof.

13. A method of treating ulcers in a subject in need of said treatment, said method comprising administering to said subject an effective amount of a compound of claim 1, wherein $R_3$ is hydroxy and $R_1$ and $R_2$ together form an oxo group.

* * * * *

UNITED STATES PATENT AND TRADEMARK OFFICE
CERTIFICATE OF CORRECTION

PATENT NO. : 4,320,143        Page 1 of 3

DATED : March 16, 1982

INVENTOR(S) : Renato Pellegata et al

It is certified that error appears in the above-identified patent and that said Letters Patent is hereby corrected as shown below:

Column 1, formula (I), in the cyclopentane ring, the upper right hand corner, change "3" to --8--.

Column 4, formula (IV), in the upper left hand corner on the cyclopentane ring, the bond connecting the oxygen to the 9 position of the ring should be a double bond, i.e. =, not a dark triangular or solid heavy line bond as shown in the patent.

Column 7, formula (V), the linkage between the carbon and oxygen in the lower side chain (to the left of $R_6$) should be a double bond, i.e. =, not a dark triangular bond as in the patent.

UNITED STATES PATENT AND TRADEMARK OFFICE
CERTIFICATE OF CORRECTION

PATENT NO.  : 4,320,143

DATED       : March 16, 1982

INVENTOR(S) : Renato Pellegata et al

It is certified that error appears in the above-identified patent and that said Letters Patent is hereby corrected as shown below:

Column 14, Table II, the correct heading of the center two columns of Table II should read:

>            Potency Ratio
>            Ileum Uterus
>             of Rats

Column 26, line 25 (claim 1 of the Patent), the comma after $R_2$ should be deleted.

Column 26, lines 26-28 (claim 1 of the patent), the quotation marks around the expression "alkanoyloyx ...group" should be deleted; and lines 25-28 should correctly read:

--bond, $R_3$ is hydroxy, and one of $R_1$ and $R_2$ is hydrogen and

UNITED STATES PATENT AND TRADEMARK OFFICE
CERTIFICATE OF CORRECTION

PATENT NO. : 4,320,143          Page 3 of 3

DATED     : March 16, 1982

INVENTOR(S) : Renato Pellegata et al

It is certified that error appears in the above-identified patent and that said Letters Patent is hereby corrected as shown below:

the other is hydroxy or alkanoyloxy group containing up to 6 carbon atoms, a benzoyloxy or a p-phenylbenzoyloxy group or $R_1$ and--.

Signed and Sealed this

Thirteenth Day of November 1984

[SEAL]

Attest:

GERALD J. MOSSINGHOFF

Attesting Officer

Commissioner of Patents and Trademarks